(12) United States Patent
Gatenholm et al.

(10) Patent No.: US 10,774,227 B2
(45) Date of Patent: Sep. 15, 2020

(54) PREPARATION AND APPLICATIONS OF BIOCOMPATIBLE CONDUCTIVE INKS BASED ON CELLULOSE NANOFIBRILS FOR 3D PRINTING OF CONDUCTIVE BIOMEDICAL DEVICES AND FOR USE AS MODELS FOR STUDY OF NEURODEGENERATIVE DISORDERS AND CONNECTION BETWEEN BRAIN/NEURONS AND COMMUNICATION OR OTHER ELECTRONIC DEVICES

(71) Applicants: Paul Gatenholm, Riner, VA (US); Erdem Karabulut, Oslo (NO)

(72) Inventors: Paul Gatenholm, Riner, VA (US); Erdem Karabulut, Oslo (NO)

(73) Assignee: CELLHEAL AS, Sandvika (NO)

( * ) Notice: Subject to any disclaimer, the term of this patent is extended or adjusted under 35 U.S.C. 154(b) by 203 days.

(21) Appl. No.: 15/963,076

(22) Filed: Apr. 25, 2018

(65) Prior Publication Data
US 2018/0305569 A1    Oct. 25, 2018

Related U.S. Application Data

(60) Provisional application No. 62/489,653, filed on Apr. 25, 2017.

(51) Int. Cl.
*C09D 11/14* (2006.01)
*C09D 11/38* (2014.01)
(Continued)

(52) U.S. Cl.
CPC .......... *C09D 11/14* (2013.01); *A61L 27/08* (2013.01); *A61L 27/20* (2013.01); *A61L 27/36* (2013.01);
(Continued)

(58) Field of Classification Search
None
See application file for complete search history.

(56) References Cited

U.S. PATENT DOCUMENTS

| 8,691,974 B2 * | 4/2014 | Gatenholm | A61L 27/20 |
| | | | 435/170 |
| 2009/0022775 A1 * | 1/2009 | Champ | A61L 27/20 |
| | | | 424/423 |

(Continued)

OTHER PUBLICATIONS

International Search Report dated Jul. 9, 2018 for PCT/US 2018/029480; 2 pages.*

(Continued)

*Primary Examiner* — Helene Klemanski
(74) *Attorney, Agent, or Firm* — Woods Rogers PLC; Nathan A. Evans (57) ABSTRACT

The present invention relates to preparation and use of nanocellulose fibrils or crystals such as disintegrated bacterial nanocellulose, tunicate-derived nanocellulose, or plant-derived nanocellulose, together with carbon nanotubes, as a biocompatible and conductive ink for 3D printing of electrically conductive patterns. Biocompatible conductive bio-inks described in this invention were printed in the form of connected lines onto wet or dried nanocellulose films, bacterial cellulose membrane, or tunicate decellularized tissue. The devices were biocompatible and showed excellent mechanical properties and good electrical conductivity through printed lines ($3.8 \cdot 10^{-1}$ S cm$^{-1}$). Such scaffolds were used to culture neural cells. Neural cells attached selectively on the printed pattern and formed connective networks. The devices prepared by this invention are suited as bioassays to screen drugs against neurodegenerative diseases such as Alzheimer's and Parkinson's, study brain function, and/or be used to link the human brain with electronic and/or communication devices. They can also be implanted to
(Continued)

replace neural tissue or stimulate guiding of neural cells. They can also be used to stimulate the heart by using electrical signaling or to repair myocardial infarction and/or damage related thereto.

17 Claims, 5 Drawing Sheets

(51) Int. Cl.
| | |
|---|---|
| C09D 11/30 | (2014.01) |
| A61L 27/08 | (2006.01) |
| A61L 27/20 | (2006.01) |
| A61L 27/38 | (2006.01) |
| A61L 27/36 | (2006.01) |
| B33Y 70/00 | (2020.01) |
| B33Y 80/00 | (2015.01) |
| C09D 11/52 | (2014.01) |
| A61L 27/44 | (2006.01) |
| C09D 11/324 | (2014.01) |
| C12N 5/00 | (2006.01) |
| C09D 11/03 | (2014.01) |
| A61L 27/50 | (2006.01) |
| C12N 5/09 | (2010.01) |
| C12N 5/071 | (2010.01) |
| A61N 1/05 | (2006.01) |
| A61N 1/36 | (2006.01) |
| A61N 1/362 | (2006.01) |
| C12N 5/0793 | (2010.01) |
| C12N 5/077 | (2010.01) |
| C09D 11/037 | (2014.01) |

(52) U.S. Cl.
CPC ......... *A61L 27/367* (2013.01); *A61L 27/3625* (2013.01); *A61L 27/3675* (2013.01); *A61L 27/3691* (2013.01); *A61L 27/38* (2013.01); *A61L 27/383* (2013.01); *A61L 27/3826* (2013.01); *A61L 27/3834* (2013.01); *A61L 27/3873* (2013.01); *A61L 27/3895* (2013.01); *A61L 27/443* (2013.01); *A61L 27/50* (2013.01); *A61N 1/0536* (2013.01); *A61N 1/362* (2013.01); *A61N 1/3605* (2013.01); *A61N 1/36067* (2013.01); *A61N 1/36082* (2013.01); *B33Y 70/00* (2014.12); *B33Y 80/00* (2014.12); *C09D 11/03* (2013.01); *C09D 11/037* (2013.01); *C09D 11/30* (2013.01); *C09D 11/324* (2013.01); *C09D 11/38* (2013.01); *C09D 11/52* (2013.01); *C12N 5/0062* (2013.01); *C12N 5/0619* (2013.01); *C12N 5/0657* (2013.01); *C12N 5/0691* (2013.01); *C12N 5/0693* (2013.01); *C12N 5/0697* (2013.01); *A61L 2300/412* (2013.01); *A61L 2300/64* (2013.01); *A61L 2400/12* (2013.01); *A61L 2430/20* (2013.01); *A61L 2430/32* (2013.01); *C12N 2501/90* (2013.01); *C12N 2501/999* (2013.01); *C12N 2513/00* (2013.01); *C12N 2533/78* (2013.01); *C12N 2539/00* (2013.01)

(56) References Cited

U.S. PATENT DOCUMENTS

| | | | |
|---|---|---|---|
| 2011/0262706 A1* | 10/2011 | Bayon ..................... | A61L 27/20 428/156 |
| 2013/0309295 A1* | 11/2013 | Gatenholm ...... | A61B 17/06166 424/444 |
| 2014/0038275 A1* | 2/2014 | Gatenholm ............. | A61L 27/20 435/288.4 |
| 2016/0144091 A1* | 5/2016 | Breedon ............... | A61F 2/0036 623/3.29 |
| 2016/0297104 A1* | 10/2016 | Guillemette ............ | B29B 11/16 |
| 2017/0087766 A1* | 3/2017 | Chung ................... | B33Y 30/00 |
| 2017/0368225 A1* | 12/2017 | Gatenholm ............. | C08B 15/08 |
| 2019/0038809 A1* | 2/2019 | Kang ..................... | C12M 25/14 |
| 2019/0060520 A1* | 2/2019 | Pelling ............... | A61L 27/3637 |
| 2019/0160203 A1* | 5/2019 | Gatenholm .......... | C12N 5/0698 |
| 2019/0209738 A1* | 7/2019 | Gatenholm ............ | A61K 35/12 |
| 2019/0282623 A1* | 9/2019 | Gatenholm ............ | A61K 35/39 |
| 2019/0307923 A1* | 10/2019 | Gatenholm ........... | B33Y 10/00 |
| 2019/0367884 A1* | 12/2019 | Satchi-Fainaro ...... | B33Y 80/00 |
| 2019/0374682 A1* | 12/2019 | Si ........................ | A61L 27/3834 |

OTHER PUBLICATIONS

Written Opinion of the International Search Authority dated Jul. 9, 2018 for PCT/US 2018/029480; 7 pages.*
Murphy et al., "3D bioprinting of tissues and organs", Nature Biotechnology, Aug. 2014, vol. 32, No. 8, pp. 773-785.*
Xu et al., "Three-Dimensional Printing of Wood-Derived Biopolymers: A Review Focused on Biomedical Applications", ACS Sustainable Chem Eng. 2018, 6, 5663-5680, no month available.*
Cui et al., "3D Bioprinting for Organ Regeneration", Advanced Healthcare Materials, Jan. 2017, vol. 6, No. 1; 29 pages.*
Markstedt et al., 3D Bioprinting Human Chondrocytes with Nanocellulose-Alginate Bioink for Cartilage Tissue Engineering Applications:, Biomacromolecules, Mar. 2015, 16, 5, pp. 1489-1496.*
European Search Report and Written Opinion, 13 pages, dated Jul. 9, 2018.
Cui et al., "3D Bioprinting for Organ Regeneration," Advanced Healthcare Materials, Dec. 20, 2016, vol. 6, No. 1, pp. 1-29. (Entire Document).

* cited by examiner

FIGURE 1. Rheological properties of Nanocellulose ink (CNF) and Nanocellulose conductive ink (CNF/CNT) at different pH.

FIGURE 2. Evaluation of printability of conductive nanocellulose ink.

FIGURE 3. Selected conductive ink patterns printed on nanocellulose support.

FIGURE 4 shows confocal microscopy images of SH-SY5Y neural network on conductive scaffold after 7 days of differentiation. Cell nuclei appear in blue; neuronal microtubules appear in green.

FIGURE 5 shows SEM image of SH-SY5Y neural cells on conductive scaffold after 7 days of culturing.

FIGURE 6 shows selective growth of neural cells on printed line with CNF/CNT conductive line.

PREPARATION AND APPLICATIONS OF BIOCOMPATIBLE CONDUCTIVE INKS BASED ON CELLULOSE NANOFIBRILS FOR 3D PRINTING OF CONDUCTIVE BIOMEDICAL DEVICES AND FOR USE AS MODELS FOR STUDY OF NEURODEGENERATIVE DISORDERS AND CONNECTION BETWEEN BRAIN/NEURONS AND COMMUNICATION OR OTHER ELECTRONIC DEVICES

CROSS-REFERENCE TO RELATED APPLICATION

The present application relies on the disclosures of and claims priority to and the benefit of the filing dates of U.S. Provisional Application No. 62/489,653, filed Apr. 25, 2017. The disclosures of that application are hereby incorporated by reference herein in their entireties.

BACKGROUND OF THE INVENTION

Field of the Invention

The present invention relates to nanocellulose- and carbon nanotubes-based biocompatible conductive inks for 3D printing. These inks are particularly suitable for 3D printing conductive patterns to provide attachment and guiding of neural cells and thus make it possible to create neural networks. Such artificial neural networks are very attractive as a model of the brain and can be used to study neurodegenerative disorders such as Alzheimer's or Parkinson's disease. They can also be used as artificial neural networks to connect the brain or neurons with external devices, such as communication devices. When the conductive inks are printed in patterns on biocompatible 3D nanocellulose support structures, such biomedical devices can be implanted and used for guiding nerves in surgery. Another application of biocompatible 3D printed conductive biomedical devices described in this invention is as cardiac devices in which the conductive pattern can be used for electrical stimulation. Such devices have therapeutic potential in engineering cardiac tissues to repair myocardial infarction.

Description of Related Art

Millions of people around the world suffer from neurodegenerative disorders such as Alzheimer's and Parkinson's disease. Alzheimer's disease (AD) is one of the costliest disorders worldwide with the total cost globally exceeding $800 billion USD in 2015 [1]. This corresponds to approximately one percent of the world GDP during the same year. The costs include diagnosing, treating and daily care of afflicted patients, which explains the high numbers. The disease causes atrophy and destruction of connections between the neurons in the brain, leading to neuron cell death. The human brain is a highly complex organ, the complexity contributing to difficulties in developing drugs and treatments for neurodegenerative diseases. Tissue engineering of the human brain with the aim to develop brain tissue models in vitro is a promising solution for development of future treatments of neurodegenerative diseases, like Alzheimer's or Parkinson's. Biocompatible and conductive scaffolds can support growth of human neurons and create brain-like neural networks in vitro. The brain-like neural networks can be used for applications to connect the brain with external devices, such as electronic devices.

Different types of scaffolds have been investigated in the field of brain tissue engineering. Jonsson et al. [2] investigated scaffolding of nanocellulose to create a 3D neural structure. Two different surface treatments were tested. The results showed that cellulose cationized with trimethyl ammonium betahydroxy propyl promoted cell attachment and proliferation, and that coatings with extracellular matrix proteins, such as collagen, improved interactions between cells and between cells and the scaffold. Cellulose as a scaffold has also been studied by Kuzmenko et al. [3]. The aim was to create a scaffold that would suit neural networks and mimic the neural extracellular matrix by making the surface of the scaffolds electrically conductive either by multiwalled carbon nanotubes or carbonization into carbon nanofibers. The study shows how the surface modification of cellulose with conductive materials enhances cell attachment compared to non-treated cellulose.

It is challenging to culture neural cells since they are dependent on attachment on the surface in order to fully differentiate. They are also dependent on neighboring neural cells to be able to develop the neural network. Nanocellulose fibrils are a potentially attractive solution as biomaterials to resolve these challenges because they absorb the water on the surfaces and form a hydrogel in a native state. Nanocellulose can be isolated from tunicates which are marine animals. Nanocellulose fibrils are also a major component of plant tissue. They can be isolated by homogenization processes and such material is called Cellulose Nanofibrils (CNF). Cellulose can be also produced by bacteria and is then called Bacterial Nanocellulose (BNC). BNC has been successfully used as implants and scaffolds in tissue engineering. In vitro and in vivo studies have shown biocompatibility of BNC implants. They did not show foreign-body reaction, fibrosis, or capsule formation [4].

Carbon nanotubes, single-walled (CWNT) or multi-walled (MWNT), are emerging nanomaterials consisting of hollow graphitic cylinders of nanoscale dimensions with unique electrical and mechanical properties. They have been combined with different synthetic and natural polymers and evaluated as scaffolds for tissue engineering.

3D printing is an emerging technology which enables a user to fabricate materials using a bottom up approach. The related technology is 3D bioprinting in which liquid biomaterial and cells are dispensed in a pattern determined with a CAD file used to control motion of a 3D bioprinter. Scaffolds for neural networks can be prepared by using a 3D printer or 3D bioprinter. The result of the biofabrication process is very much dependent on inks. Inks have the crucial role of providing suitable rheological properties during the 3D printing process, which affect fidelity of the printed pattern and also in the later stages when the inks act as scaffolds during tissue development.

SUMMARY OF THE INVENTION

In aspects of this invention, a preparation of biocompatible conductive inks composed of nanocellulose fibrils or nanocrystals, such as disintegrated bacterial cellulose or nanocellulose isolated from tunicates or primary or secondary cell wall of plants with addition of carbon nanotubes, is taught; using them for 3D printing electrically conductive patterns is also described. Conductive bioinks, after deposition/printing, provide attachment sites and guidance for neural cells and can thus control formation of neural networks. In one aspect, the invention uses BNC, which is an electrical isolator, as a substrate for printing. The advantage of using nanocellulose as a substrate is a combination of beneficial mechanical properties, along with biocompatibility coupled with lack of cell attachment. The neural networks formed on conductive inks can be used as a model of the brain to study neurodegenerative disorders such as Parkinson's and Alzheimer's disease. They can also be used as brain-like neural networks to link the human brain or neurons with communication devices. The nanocellulose as a printing substrate can be used as wet membrane or printed and dried. Bacterial nanocellulose or tunicate derived nanocellulose are preferable for use as printing substrates. Such a biocompatible conductive device can be implanted in the heart to stimulate cells to repair the heart, or to use to send or facilitate electrical signals for controlling heart beating, functionality, or viability. Such implantable devices can also be used for guides for neural tissue repair.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION OF VARIOUS EMBODIMENTS OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties.

EXAMPLE 1

Preparation and Characterization of Biocompatible Conductive Inks

Bacterial Cellulose Cultivation

Cultures of the strain G. xylinus subsp. Sucrofermentans BPR2001, trade number: 700178, purchased from the American Type Culture Collection were maintained on complex media as described by Matsuoka et. al [5]. Nanocellulose scaffolds were grown with 0.2 mL of bacterial preculture (containing 2 million bacteria as determined by OD600 nm) added to the 2 mL medium in the wells of a cell cultivation plate that was incubated in a bacteriological cabinet at 30° C. for 3 days. The cellulose pellicles formed were then washed in two successive 0.1M NaOH baths at 60° C. for 7 days each, followed by two washes in distilled water at 60° C. for 1 day followed by washing in pyrogen-free water. Finally, all cellulose pellicles were autoclaved in water before use.

Homogenization of BNC a) Hydrolysis was carried out by treating 100 g of BNC gel (1 g cellulose) with 19 wt. % sulfuric acid at 60° C. for 48 h, after which the reaction system was cooled and neutralized with 1 M NaOH. The sample was then washed thoroughly with de-ionized water and centrifuged at 4000 rpm for 15 minutes at least 5 times. The obtained gel was then re-suspended in 300 ml pyrogen-free water (HyClone cell culture-grade water, Thermo Fisher Scientific) and treated with an UltraTurrax (IKA) at 20,000 rpm for 10 minutes. The obtained colloidal dispersion was then centrifuged at the same conditions as above. The gel was further concentrated to 5 wt. % by means of ultrafiltration with a UF unit (Waters) and a PTFE membrane of 1000 MWCO.

b) Mechanical homogenization: BNC pellicles were cut into small pieces, disintegrated in a lab blender and homogenized at 20,000 rpm (0.4 wt. % concentration) with an Ultraturrax (IKA) at 20,000 rpm for 5 minutes, and then submitted to ACC treatment (using ACC system Sugino, Japan) at 200 MPa of ejecting pressure 30 times (pass).

Conductive Inks Preparation

Bacterial Nanocellulose (BNC) aqueous dispersion (2.4 wt. %) was diluted in water for better homogenization. Aqueous SWCNT dispersion (1 wt. %, 10 mL, Carbon Solutions, Inc., purified with nitric acid P3-SWNT, bundle diameter 4-5 nm, 1.0-3.0 at. % $COO^-H^-$) was added and homogenized at 8,000 rpm with UltraTurrax mixer (IKA, T25basic, S25N8G) for 10 minutes. The resulting mixture had BNC/CNT dry weight ratio of 80/20 and the concentration of 0.2 wt. %. 1 M NaOH wad added until the pH of the dispersion reached from pH 6.5 to pH 8.5 to gain a better miscibility between two components. The mixture was homogenized again with UltraTurrax mixer for 10 minutes at 8,000 rpm. Yet the mixture was too diluted for printing. Therefore, it was dehydrated by two consecutive steps: 1) centrifugation at 4,000 rpm with a subsequent removal of a clear supernatant; 2) air-drying for 3 days. Final concentration of printable inks was 2 wt. %. For comparative analysis, the inks made of the pure 2 wt. % BNC were also prepared.

Another ink prepared in this study was based on carboxymethylated CNF isolated from wood. The conductive CNF/CNT ink was prepared using the same experimental procedure as for BNC ink.

Figure 1:
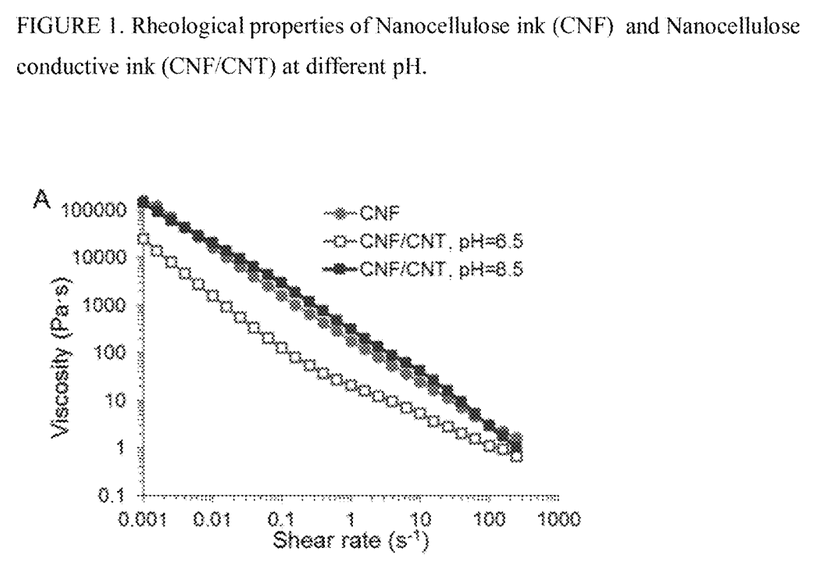
FIG. 1. Rheological properties of CNF ink and Nanocellulose conductive ink (CNF/CNT) at different pH.

The inks were characterized using rheological measurements. FIG. 1 shows the effect of shear rate on viscosity for CNF ink and CNF/CNT ink at pH 6.5 and pH 8.5. All the inks show preferred shear thinning behavior for preferred printability. They also show high viscosity at low shear rate which is important for gelling after printing. The addition of CNT resulted in decreased viscosity at pH 6.5. Viscosity was, however, increased when pH was increased to pH 8.5.

EXAMPLE 2

3D Printing and Solidification of Conductive Scaffolds

Figure 2:
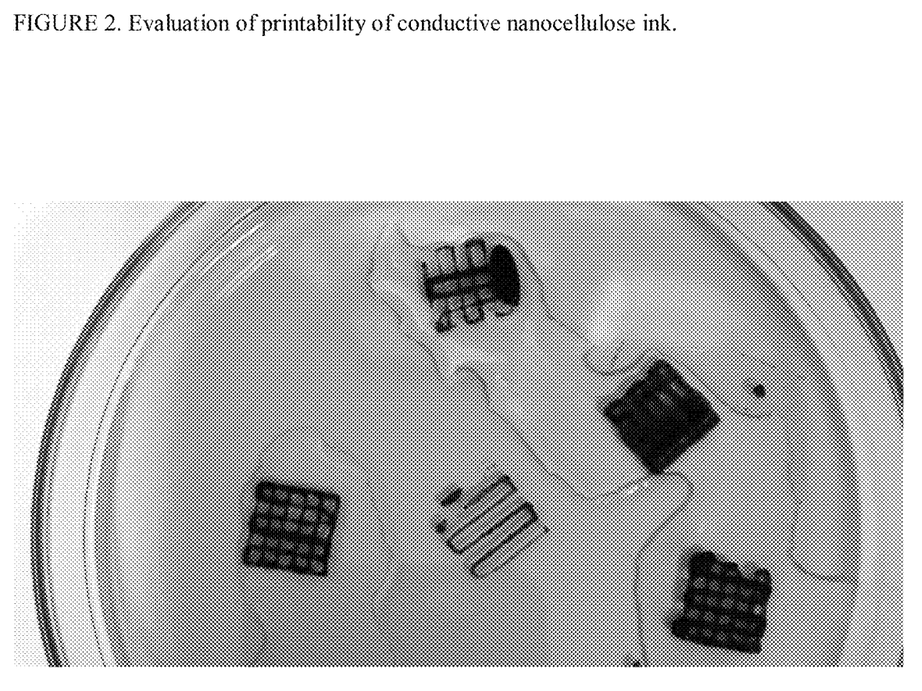
FIG. 2. Evaluation of printability of conductive nanocellulose ink.
Figure 3:
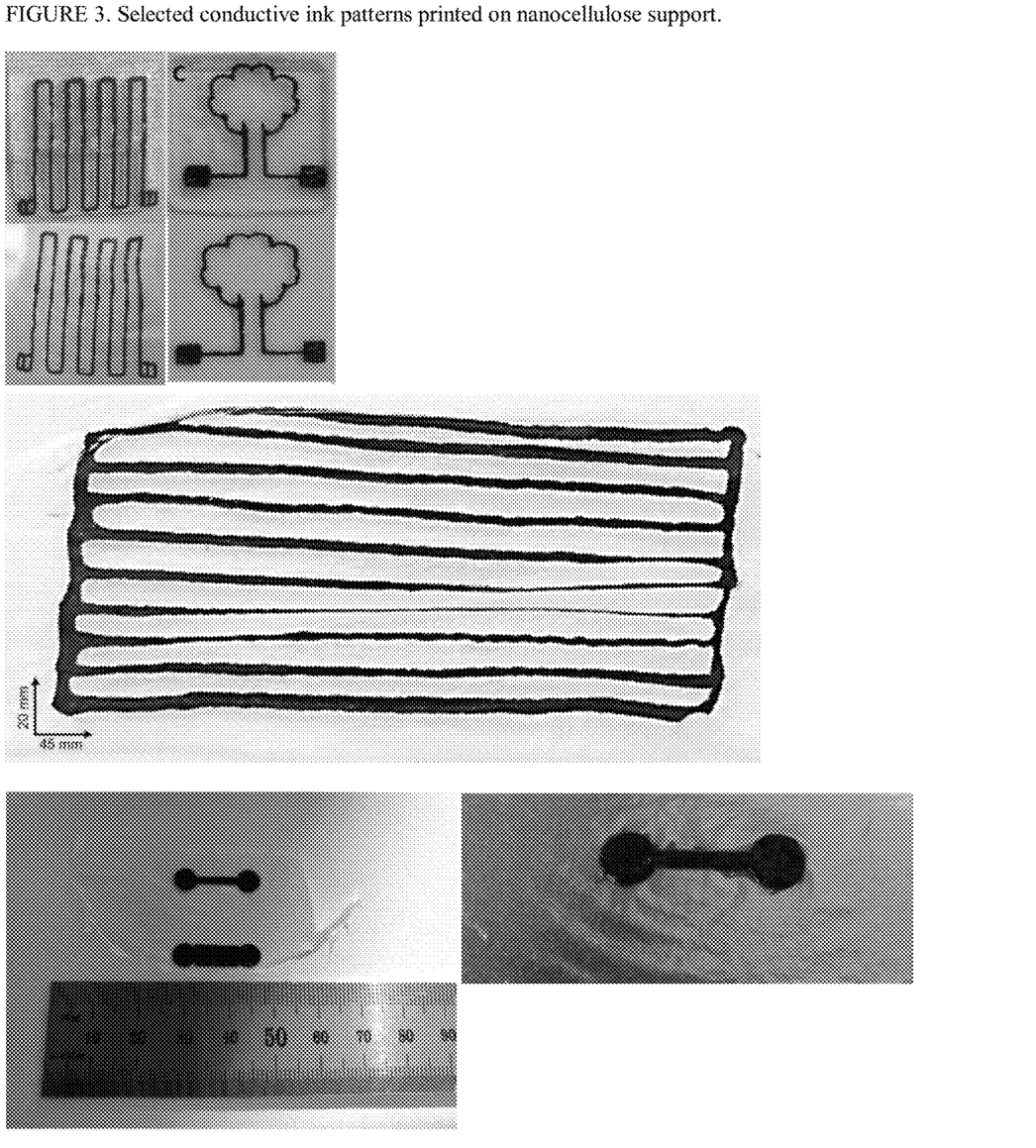
FIG. 3. Selected patterns printed on nanocellulose support.

3D Printing 3D bioprinter (3D Discovery from RegenHU, Switzerland) was used to print 3D scaffolds using an ink jet printing head equipped with a piezoelectric microvalve and a 300 µm nozzle. Printability of conductive bioinks was tested by printing different patterns as it is shown in FIG. 2. When printing without nanocellulose support the lines were not well resolved and it was observed that the carbon agglomerates were not in continuous phase. In one aspect, it was selected in this invention to use dried nanocellulose as a substrate for printing conductive pattern(s). The nanocellulose substrates can be obtained by printing nanocellulose ink and drying, by casting nanocellulose gel, or by drying bacterial cellulose pellicles. The latest one provided a substrate with preferable mechanical properties and biocompatibility. The dried bacterial cellulose pellicle will swell in wet conditions depending on the conditions in which the pellicle was dried. Drying at elevated temperatures (e.g., more than 100 degrees° C.) for a sufficiently long period of time (e.g., more than 1 hour) results in nanocellulose film which swells to a preferred degree. Selected conductive patterns were designed using BioCAD software. The patterns were printed at the dispensing pressure of 65 kPa pressure, the valve opening time of 1200 µs, the dosing drop distance of 0.05 mm, and the printing speed of 10 mm s$^{-1}$. Under these conditions, around 1 minute was needed to print a single batch of 6-8 scaffold samples (see FIG. 3). At the end of the process, scaffolds were air-dried at ambient conditions for 24 hours. Nanocellulose films with a thickness around 35 µm were used as substrates for 3D printed scaffolds. The conductive lines were now cohesive compared to lines printed without nanocellulose support.

Electrical Conductivity

The measurements were performed along the 3D printed patterns at dry state using a two-point probe system (22° C., Parameter Analyzer-Keithley 4200-SCS). The distance between the probes was kept at around 2 mm during the measurements at different spots. The calculation of an average conductivity value was based on five measurements. Homogeneous dispersion of 20 wt. % CNTs in nanocellulose hydrogel made the ink suitable for printing guidelines with electrical conductivity of around $3.8 \cdot 10^{-1}$ S cm$^{-1}$. In contrast, pure nanocellulose film is an isolator with electrical conductivity around $1 \cdot 10^{-6}$ S cm$^{-1}$. Pure CNT film has conductivity of around 34 S cm$^{-1}$.

EXAMPLE 3

Culturing Neural Cells onto Conductive Devices

Cell culturing: The SH-SHY5Y human neuroblastoma cells (Health Protections Agency Culture Collections, HPACC, Catalogue No. 94030304) were expanded until passage 22 in growth medium consisting of equal amounts of minimum essential medium (MEM, Life Technologies, USA) and Ham's Nutrient mixture F-12 (Life Technologies), supplemented with non-essential amino acids (1%, PAA Laboratories), GlutaMax (1%, PAA Laboratories), antibiotic-antimycotic (1%, Life Technologies) and heat-inactivated fetal calf serum (10%, Hyclone) [6]. The differentiation medium had a lower serum concentration (1%) and was additionally supplemented with retinoic acid (10 µM, Sigma Aldrich). Cells were maintained in humidified atmosphere at 37° C. and 95% air/5% $CO_2$. For differentiation studies, scaffolds were cut into 1 cm$^2$ samples, placed under rubber rings in 24-well plates, sterilized in ethanol (70%) for 40 minutes and then washed five times in PBS. The samples were incubated with growth medium for 1 hour before seeding cells at densities of $2 \cdot 10^4$ or $10^5$ cells/sample depending on the type of analysis. One day after seeding, the growth medium was replaced with differentiation medium and cells were cultured for up to 27 days, with 70% medium changes 3 times a week.

Cell viability: Possible cytotoxic effects from the CNT-ink were investigated by an extraction-based cytotoxicity assay evaluated using the AlamarBlue® Cell Viability Reagent (Invitrogen). Extraction was performed by submerging 1 cm$^2$ samples into complete culture medium (500 µL) at 37° C. for 24 hours. SH-SY5Y cells were seeded in complete culture medium (100 µL) at the cell density of $2 \cdot 10^4$ cells/well in a 96-well plate. After 24 hours in cell incubator the medium was aspirated and replaced by the extraction medium. As an assay blank, complete medium was used. As a negative control, medium incubated with a plastic piston was used, and medium with TritonX (0.1%) was used as positive control. After 24 hours incubation, the AlamarBlue® Reagent (10 µL) was added to each sample including blanks containing only medium. After 20 hours the absorbance was measured at 570 nm wavelength using a plate reader (Epoch, BioTek). The data was analyzed using the Gen5 software. The viability was calculated as a ratio between the blank/positive control and the sample absorbance.

A Live/Dead cell viability assay was performed using the LIVE/DEAD® Cell Imaging Kit (Life Technologies). Samples were washed in warm transparent MEM and incubated with the live/dead staining solution prepared according to the manufacturer's guidelines for 15 minutes at room temperature. The cell density of $10^5$ cells/well in a 96-well plate was used for the assay. Visualization was performed using an inverted epifluorescence microscope (IX73, Olympus) equipped with a 10× objective. Standard FITC and Texas Red filters were used to identify live (green) and dead (red) cells, respectively. 100% or preferable cell viability was found.

Confocal microscopy: The cytoskeleton and nuclei were stained for cells differentiated for 1, 10 and 27 days to visualize cell morphology and attachment. Samples were fixated in formalin (4%) for 15 minutes, washed in PBS and stained with ActinGreen™ 488 ReadyProbes® Reagent for 30 minutes and NucBlue® Fixed Cell Stain (DAPI) for 10 minutes. Solutions were prepared according to the manufacturer's instructions. A confocal laser scanning microscope (LSM 710 NLO, Carl Zeiss) with a W Plan-Apochromat 20× objective was used to acquire fluorescence images. Due to the topography of the samples, Z-stacks of 32 µm thickness were obtained with a 3.2 µm interval. Images were produced using the ZEN Black Edition imaging software.

Figure 4:
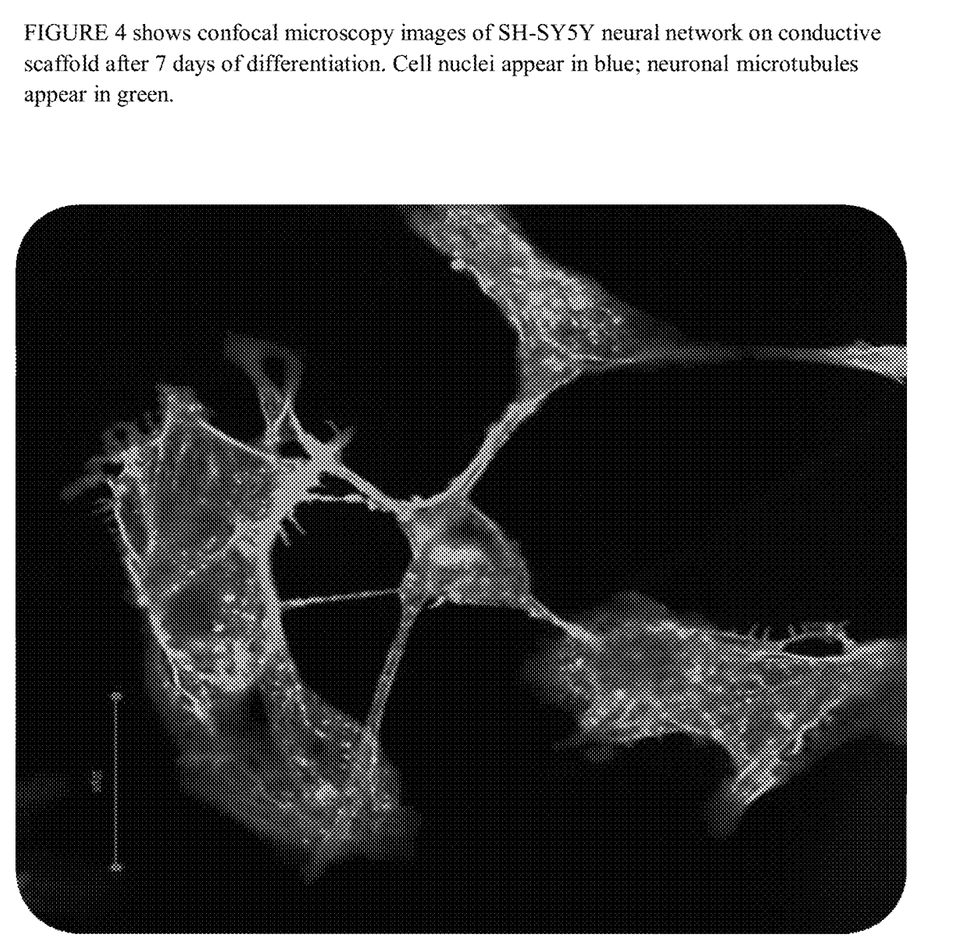
FIG. 4. Confocal microscopy images of SH-SY5Y neural network on conductive scaffold after 7 days of differentiation. Cell nuclei appear in blue; neuronal microtubules appear in green.

FIG. 4 shows confocal microscopy images of SH-SY5Y neural network on conductive scaffold after 7 days of differentiation. Cell nuclei appear in blue; neuronal microtubules appear in green.

Figure 5:
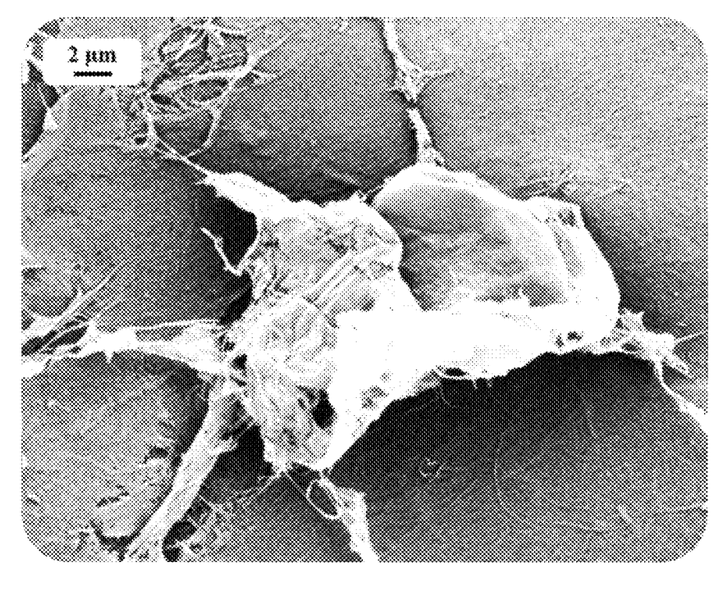
FIG. 5. SEM image of SH-SY5Y neural cells on conductive scaffold after 7 days of culturing.
Figure 6:
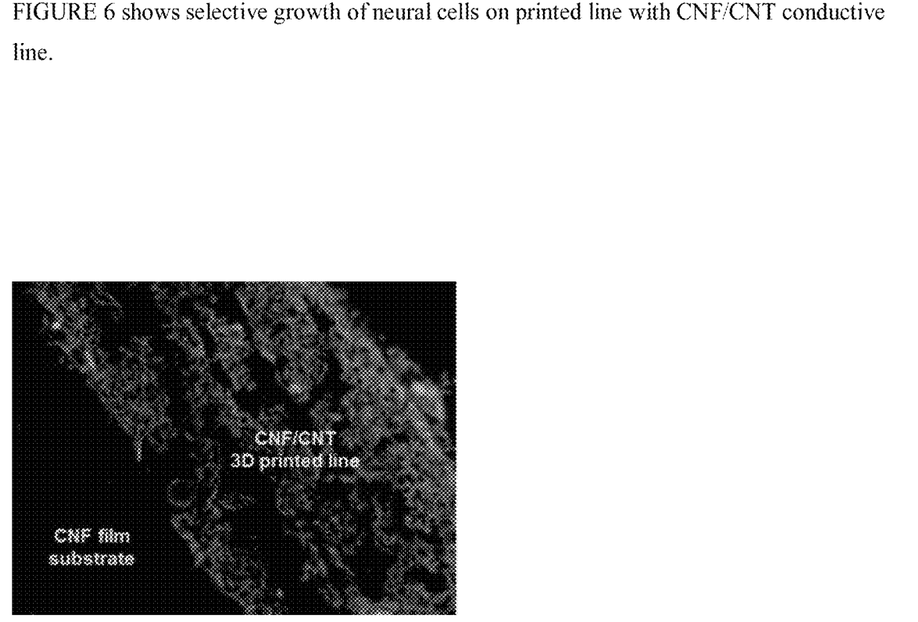
FIG. 6. Selective growth of neural cells on printed line with CNF/CNT conductive line.

Scanning electron microscopy (SEM): A scanning electron microscope (LEO Ultra 55 FEG SEM Zeiss) was operated at an acceleration voltage of 3 kV in secondary electron mode. Prior to microscopy analysis, all samples were sputter-coated with 10 nm thick gold layer in a vacuum at 10 mA for 80 seconds (Fine Coat Ion Sputter JFC-1100, JEOL Ltd., Tokyo, Japan). Scaffolds with cultured cells were fixated in glutaraldehyde (2%) for 1 hour, rinsed with PBS and dehydrated in a series of increasing ethanol concentrations. SEM micrograph in FIG. 5 shows an image of SH-Sy5Y neural cells on a conductive scaffold after 7 days of culturing. Cells were observed to adequately attach to the conductive ink. There was no cell attachment to pure nanocellulose surface(s). FIG. 6 shows experimental results where the lines with conductive CNF/CNT ink were printed on CNF dried substrate. The neural cells attached selectively only to conductive lines, proliferated and formed a network.

EXAMPLE 4

Use of the Conductive Device to Stimulate Heart and Repair Myocardianl Tissue after Infarct 3D printed scaffolding based on bacterial cellulose pellicle with 3D printed conductive pattern with conductive ink was evaluated to repair myocardial tissue (heart) after infarct. Cardiac cells were isolated from 1-day-old neonatal Sprague-Dawley rats and seeded onto 3D scaffolds to construct a 3D tissue model (100 000 cells/ml). The models were cultured under static conditions for 3 days, following 5 days' electrical field stimulation to enhance electrical performance. The cell constructs were cultivated in an incubator (37 degrees 5% CO2), under electrical stimulation (rectangular, 3 ms pulse, 5 V, 5 V/cm, 1 Hz). The cells attached, proliferated and formed an interconnective network(s). This conductive device can be integrated to infarct myocardium and provide beneficial effects on the myocardial regeneration and remodeling in the infarct areas, resulting in the improvement of heart function.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

References Noted Above and Incorporated Herein By Reference

1. M. Prince, A. Wimo, M. Guerchet, G.-C. Ali, Y.-T. Wu, M. Prina, *World Alzheimer Report* 2015. *The Global Impact of Dementia*, Alzheimer's Disease International (ADI), London, 2015.
2. Jonsson M, Brackman C, Puchades M, Brattås K, Ewing A, Gatenholm P, et al. Neuronal Networks on Nanocellulose Scaffolds. TISSUE ENGINEERING: Part C. 2015 September; 21(11):1162-1170.
3. Kuzmenko V, Kalogeropoulos T, Thunberg J, Johannesson S, Hägg D, Enoksson P, et al. Enhanced growth of neural networks on conductive cellulose-derived nanofibrous scaffolds. Materials Science and Engineering C. 2015, 58:14-23.
4. G. Helenius, H. Bäckdahl, A. Bodin, U. Nannmark, P. Gatenholm, B. Risberg, In vivo biocompatibility of bacterial cellulose, J.Biomed.Mater.Res. A76 (2006) 431-438.
5. Matsuoka M, Tsuchida T, Matsushita K, Adachi O, Yoshinaga F. A synthetic medium for bacterial cellulose production by Acetobacter xylinum subsp sucrofermentans. Biosci Biotech Biochem 1996;60:575-579.
6. M. Innala, I. Riebe, V. Kuzmenko, J. Sundberg, P. Gatenholm, E. Hanse, S. Johannesson, 3D Culturing and Differentiation of SH-Sy5Y Neuroblastoma Cells on Bacterial Nanocellulose Scaffolds, *Artif. Cells, Nanomed., Biotechnol.* 2014,42, 302-308.

The invention claimed is:

1. A biocompatible and electrically conductive three-dimensional printing ink comprising nanocellulose dispersed in water, the nanocellulose comprising hydrolyzed or disintegrated bacterial cellulose, nanocellulose fibrils, nanocellulose nanocrystals, disintegrated bacterial cellulose, nanocellulose isolated from tunicates, and/or nanocellulose isolated from plants, with or without the addition of carbon nanotubes, capable of forming three-dimensional electrically conductive patterns.

2. The biocompatible and electrically conductive three-dimensional printing ink of claim 1, wherein the biocompatible and electrically conductive three-dimensional printing ink comprising nanocellulose dispersed in water is used to three-dimensional print the electrically conductive patterns onto biocompatible nanocellulose three-dimensional substrate support(s), wherein the resulting product is biocompatible and electrically conductive.

3. The biocompatible and electrically conductive three-dimensional printing ink of claim 1, wherein the three-dimensional electrically conductive patterns are used for culturing neural cells to form neural networks.

4. The biocompatible and electrically conductive three-dimensional printing ink of claim 1, wherein the three-dimensional electrically conductive patterns are used for drug discovery or testing treatments or to be used as a neurodegenerative disease model.

5. The biocompatible and electrically conductive three-dimensional printing ink of claim 1, wherein the three-dimensional electrically conductive patterns are used for culturing induced pluripotent stem cells, mesenchymal stem cells, neuroprogenitor cells, and/or neural cells, to form neural networks.

6. The biocompatible and electrically conductive three-dimensional printing ink of claim 1, wherein the three-dimensional electrically conductive patterns are used for culturing neural cells to form neural networks and is used to link the brain or neurons with an electronic or communication device, chosen from one or more of the following: a phone, a cellular phone, a computer processing unit, a computer, a display screen, and/or a wireless device.

7. The biocompatible and electrically conductive three-dimensional printing ink of claim 3, wherein living neural tissue is used for culturing neural cells to form neural networks.

8. The biocompatible and electrically conductive three-dimensional printing ink of claim 3, wherein living neural tissue is used for culturing neural cells to form neural networks, which are implanted in a human or animal.

9. The biocompatible and electrically conductive three-dimensional printing ink of claim 5, wherein living neural tissue is used to form the neural network, which is implanted in a human or animal.

10. The biocompatible and electrically conductive three-dimensional printing ink of claim 1, wherein the three-dimensional electrically conductive patterns are capable of treating animals and/or humans suffering from a tissue defect by implanting the three-dimensional electrically conductive patterns in or on the animals and/or humans suffering from the tissue defect.

11. The biocompatible and electrically conductive three-dimensional printing ink of claim 1, wherein the three-dimensional electrically conductive patterns are capable of treating animals and/or humans by replacing brain, heart, and/or neural tissue, and/or by implanting in or around brain, heart, and/or neural tissue.

12. The biocompatible and electrically conductive three-dimensional printing ink of claim 1, wherein the three-dimensional electrically conductive patterns are capable of treating animal and/or human organs by providing electrical impulses to the three-dimensional electrically conductive patterns.

13. The biocompatible and electrically conductive three-dimensional printing ink of claim 1, wherein the three-dimensional electrically conductive patterns are capable of treating animal and/or human organs by implanting the three-dimensional electrically conductive patterns into or onto the heart and/or heart tissue and stimulating heart cells to grow and repair and/or treat myocardial infarction, damage caused by myocardial infarction, and/or other heart pathology.

14. The biocompatible and electrically conductive three-dimensional printing ink of claim 2, wherein the biocompatible nanocellulose three-dimensional substrate support(s) are used as a wet membrane or are printed and dried.

15. The biocompatible and electrically conductive three-dimensional printing ink of claim 2, wherein the biocompatible nanocellulose three-dimensional substrate support(s) comprise bacterial nanocellulose, tunicate-derived nanocellulose, and/or plant-derived nanocellulose.

16. The biocompatible and electrically conductive three-dimensional printing ink of claim 12, wherein the animal and/or human organs comprise a heart, a brain, or both.

17. The biocompatible and electrically conductive three-dimensional printing ink of claim 13, wherein the animal and/or human organs comprise a heart.

* * * * *